United States Patent [19]

Lupton et al.

[11] Patent Number: 5,155,042
[45] Date of Patent: Oct. 13, 1992

[54] BIOREMEDIATION OF CHROMIUM (VI) CONTAMINATED SOLID RESIDUES

[75] Inventors: F. Stephen Lupton, Evanston; Louis J. DeFilippi, Prospect; James R. Goodman, Chicago, all of Ill.

[73] Assignee: Allied-Signal Inc., Morris Township, Morris County, N.J.

[21] Appl. No.: 504,448

[22] Filed: Apr. 3, 1990

Related U.S. Application Data

[63] Continuation-in-part of Ser. No. 177,554, Apr. 4, 1988, abandoned.

[51] Int. Cl.$^5$ .............. C12P 1/04; C12N 1/36; C02F 3/00
[52] U.S. Cl. .................... 435/262.5; 435/170; 435/245; 435/821; 210/601; 210/610; 210/611; 588/256
[58] Field of Search .............. 435/170, 174, 176, 245, 435/262.5, 821; 210/601, 610, 611; 588/256

[56] References Cited

U.S. PATENT DOCUMENTS

| | | | |
|---|---|---|---|
| 3,941,691 | 3/1976 | Romanenko et al. | 210/2 |
| 4,468,461 | 8/1984 | Bopp | 435/253 |
| 4,477,570 | 10/1984 | Colaruotolo et al. | 435/262 X |
| 4,522,723 | 6/1985 | Kauffman et al. | 210/611 |
| 4,704,259 | 11/1987 | Lipsztajn | 423/55 |
| 4,761,376 | 8/1988 | Kulpa et al. | 435/262 |
| 4,789,478 | 12/1988 | Revis et al. | 210/611 |

OTHER PUBLICATIONS

R. H. Smillie, K. Hunter & Margaret Loutit, "Reduction of Chromium (VI) by Bacterially Produced Hydrogen Sulphide in a Marine Environment Water Research", 15, 1351–54 (1981).

*Primary Examiner*—David M. Naff
*Attorney, Agent, or Firm*—Eugene I. Snyder; Harold N. Wells; Gerhard H. Fuch

[57] ABSTRACT

Chromium in solid waste residues may be immobilized by reduction of essentially all of the Cr(VI) to insoluble Cr(III). The Cr(VI) is separated from the solids by contacting with an acid to produce an aqueous solution having a pH of about 6.5 to 9.5, then adding sulfate-reducing anaerobic bacteria and, as required, a source of sulfates and nutrients for the growth of the bacteria. Where the solid residues are below the surface of the soil, a continuous recirculation may be established to extract Cr(VI), treat the resulting solution above grade to reduce Cr(VI) to Cr(III), and return the treated solution to the soil.

16 Claims, No Drawings

BIOREMEDIATION OF CHROMIUM (VI) CONTAMINATED SOLID RESIDUES

CROSS-REFERENCE TO RELATED APPLICATION

This application is a continuation-in-part of U.S. Ser. No. 07/177,554, filed Apr. 4, 1988, now abandoned.

BACKGROUND OF THE INVENTION

One of the hallmarks of contemporary civilization is that each increment of technological progress almost invariably is accompanied by a similar increment of environmental regress. As the pace of technological advances quickens so does the march of environmental deterioration. The realization of environmental damage has occurred only relatively recently, so that present society finds itself burdened with the accumulated sins of the not-too-distant past. Many such burdens manifest themselves as toxic waste sites, i.e., geographical areas formerly used indiscriminately, or without recognition of inherent dangers, as dumps for waste materials and which now contain concentrations of one or more materials inimicable to the continued health of humans and of the environment generally.

A hallmark of current society is its acceptance of the undesirability of environmental degradation coupled with a determination to minimize it and reverse it wherever possible. A first step is the identification of potentially toxic sites and the materials which render such sites hazardous. A next step is the identification of methods and procedures which can render such sites at least environmentally neutral. Because the problems associated with toxic wastes are relatively new solutions for cleaning up such sites often are wanting or incomplete. The current surge in activity in developing adequate procedures for neutralizing toxic waste sites is a response to the new awareness of the undesirability of such dumps as well as an emerging determination to reverse the environmental trends of the past.

One kind of hazardous waste arises from the chromium roasting process, where chromium in iron-containing ore is oxidized to chromates to enable separation of the water-soluble chromates from insoluble ferric oxide. The residues from the aforementioned process contain chromate—more generally Cr (VI)—usually in a highly alkaline environment arising from contamination with rather high levels of lime (CaO), which is used in large quantities in the chromium ore roasting process. It is not unusual for Cr (VI), analyzed as chromium, to be present at such sites in concentrations of 20,000 ppm. Since Cr (VI) is toxic at levels of about 5 ppm to humans such residues present an immediate hazard to animals and an indirect hazard via the normal food chain to humans. Additionally, permeation of water through the solid residues with continual leaching of Cr (VI) threatens contamination of the subsurface water which could render wells impotable and adversely affect marine life.

The naturally occurring reduction of Cr (VI) to Cr (III) by hydrogen sulfide produced by sedimentary bacteria previously has been noted by R. H. Smillie, K. Hunter, and M. Loutit, "Reduction of Chromium (VI) by Bacterially Produced Hydrogen Sulfide in a Marine Environment," Water Research, 15. 1351 (1981). However, it is believed that sulfate-reducing bacteria were considered to be unsuitable for treating chromium-containing industrial waste waters because of the inherent toxicity of chromium to microoorganisms, as the following prior art indicates.

Revis et al. in U.S. Pat. No. 4,789,478 provide a brief discussion of many prior art patents pertaining to removal of heavy metals from waste waters using microorganisms, but omit reference to the reduction of Cr(VI).

In U.S. Pat. No. 4,522,723 Kauffman et al. disclose a process for reducing the concentration of water soluble ionic heavy metal species and sulfate ions in aqueous wastes. Although their principal interest appears to be in reducing uranium and molybdenum in mining waste waters, Kauffman et al. suggest the method can be employed with metal ions from many groups of the Periodic Table, including Group VIb, which contains chromium. However, there is no indication that the patentees' method had been applied to chromium-containing waters from industrial waste waters or solid residues in contact with such waters where the concentrations of chromium and other ionic species are very high. Such waters are particularly difficult to treat since they inhibit or are toxic to sulfate-reducing bacteria.

Romanenko et al. in U.S. Pat. No. 3,941,691 are consistent with Kauffman et al. and state that sulfates may be reduced to $H_2S$, which then reacts with soluble iron to form insoluble iron sulfides using sulfate reducing bacteria. However, they state that Desulfovibro desulfuricans bacteria, which are one species of sulfate reducing bacteria, are not capable of reducing chromates and bichromates. Instead, their invention resides in the selection of a microorganism which directly reduces the chromates and bichromates to chromium hydroxides without forming hydrogen sulfides.

Bopp, in U.S. Pat. No. 4,468,461 also discloses a new bacteria strain especially intended to remove chromates from waste water. In contrast with Kauffman et al. who used bacteria to produce $H_2S$ which thereafter reduced the dissolved metals and presumably precipitated them as the metal sulfide, the microorganism used by Bopp directly reduced $Cr^{+6}$ to $Cr^{+3}$ and had resistance to the poisoning effect of dissolved chromium. In fact, the patentee states that his microorganism is capable of reducing $Cr^{+6}$ up to 2000 ppm while other bacteria would not grow in concentrations more than 10-20 ppm. The microorganism is stated to be able to grow in either aerobic or anaerobic conditions, although aerobic conditions appear to be preferred. An organic reducing agent is required to satisfy the nutritional requirements of the microorganisms.

THE PROBLEM AND ITS SOLUTION

This application is directed toward immobilization of Cr (VI) dissolved in solid residues. By "immobilization" is meant reducing the soluble Cr (VI) level while transforming the remainder of the originally soluble Cr (VI) to an insoluble form of chromium which is sufficiently resistant to leaching as to enable the solid residue to pass the EPA extraction procedure toxicity test, method 1310, thereby minimizing environmental hazards. This test method as adapted for the extraction of chromium containing wastes is set forth in detail below.

The method of our invention basically involves growing hydrogen sulfide-producing anaerobes in the solid wastes containing unacceptably high levels of chromium. What happens is that Cr (VI) is reduced to Cr (111) which precipitates as the hydroxide, an extremely insoluble species, within the pH range at which fermentation is conducted. The Cr (III) hydroxide is very stable and quite resistant to leaching so that the leachate therefrom is very low in chromium, in fact sufficiently low as to pose virtually no environmental hazard.

However simple may be the statement of the problem and the broad outlines of its solution, the particulars of that solution are complicated by some characteristics inherent in the residue. The solid is highly alkaline, and therefore not amenable to bacterial growth. Because of the high calcium levels in the residue, acidification with many acids leads to formation of nonporous calcium salts which tend to clog the residue, rendering subsequent liquid permeation and microbial penetration difficult at best. Additionally, lime tends to be neutralized in stages, leading to alkali rebound. That is, after an initial pH reduction the pH gradually climbs back into the highly alkaline range. Therefore, the kind of acid used, its concentration of application, how it is applied and the schedule of its application need to be carefully unraveled and coordinated. Once the pH is reduced to the range between about 6.0 and 9.5 to permit growth of suitable anaerobic microorganisms, it is observed that both the high Cr (VI) and continually increasing pH make continued growth impossible. It is further observed that a viable, self-sustaining population of active anaerobes can not be maintained until the soluble Cr (VI) level is reduced to approximately 200 ppm and the pH of the solid residues remain within a defined pH range. Therefore, it is necessary to schedule the application of anaerobic microorganisms to the contaminated solid residues, possibly with ancillary treatment to aid in the immediate reduction of Cr (VI) levels to the point where a self-sustaining population of anaerobic microorganisms becomes more readily feasible. As a further complicating consideration the manner of treatment both by acid and by anaerobic microorganisms may be important in the effective immobilization of Cr (VI) throughout all strata of the contaminated solid residue.

SUMMARY OF THE INVENTION

An object of this invention is to immobilize soluble Cr (VI) in calcium containing solid residues from chromium ore roasting and where the residue after treatment is sufficiently resistant to leaching so as to contain less than 0.05 milligrams per liter of hexavalent chromium according to the Environmental Protection Agency Extraction Procedure (EP) Toxicity Test Method 1310, EPA Publication SW-846 as adapted for soluble chromium and described hereinafter.

In one embodiment the invention comprises contacting the solid residue with an acid which reduces pH to about 6.5 to 9.5 thereby dissolving Cr(VI) and producing a soluble calcium compound by reaction with the solid residue. Fermentative sulfate-reducing anaerobic bacteria capable of tolerating high salinity are added along with a sulfate source sufficient to provide at least 10 millimoles of sulfate per liter of aqueous solution, and sufficient nutrients to support the growth of the bacteria. The reduction of Cr(VI) is continued until the desired degree of conversion to Cr(III) has been obtained, preferably until substantially all of the Cr(VI) has been converted, which may be down to about 0.05 ppm Cr(VI) as chromium in solution. Hydrochloric acid is preferred for dissolving Cr(VI) and adjusting the pH of the aqueous solution. Alternatively, the acid may be an organic acid, such as acetic or lactic acid.

The process of the invention may be applied where soluble Cr(VI) compounds are found under the surface of the soil and is particularly useful where the Cr(VI) is tied up by the lime residues resulting from chromium ore roasting. The Cr(VI) is freed from the lime by acid treatment and the resulting solution is contacted with sulfate-reducing anaerobic bacteria to reduce essentially all of the Cr(VI) to a soluble Cr(III). A continuous circulation may be established through the affected soil whereby the Cr(VI) is dissolved and separated as an aqueous solution, treated above-grade, and then the solution containing active bacteria is returned to the soil where further treatment may occur.

TOXICITY CHARACTERISTIC LEACHING PROCEDURE (TCLP)

The method used is described in detail below and has been adapted directed from the Federal Register, Vol. 51, No. 114, pp. 21648–21693, esp., pp. '85–92, Jun. 13, 1986.

Reagents

Nitric acid, HCl and NaOH, all 1.0 -N; glacial acetic acid; all ACS Reagent grade. We use deionized reverse osmosis (DIRO) water.

Materials

1. Glass fiber filters (see below).
2. 4.7 cm three piece filter funnel (Whatman #1950-004).
3. Extraction vessel: 60 mL polypropylene vial with leak proof screw on cap (Cole-Parmer J-6075-40, polyethylene, 60 mL vol.).
4. Roto torque machine (heavy duty rotator, Model 7637, Cole-Parmer Instrument Co.) fitted with a Model 7637-75 sample holder.
5. Magnetic stir plates.
6. Magnetic stir bars.
7. Various sized borosilicate beakers fitted with watch glasses.

Glass fiber (borosilicate) filters and filter holders

The filters must have an effective pore size of 0.6–0.8 $\mu$m. We use 0.7 micron retention, 47 mm diameter, Whatman GF/F glass fiber filters. They must be acid washed prior to use. Acid wash procedure: Place about 25 to 50 of the filters in a cut-down, acid-washed, two liter Erlenmeyer flask. Add 250 mL of 1.0N nitric acid Cover with Saran Wrap TM or parafilm and slowly agitate (60 to 120 RPM) on an orbital shaker for 30 min. Remove the nitric acid by draining and rinsing four times with the DIRO water (minimum of 500 mL per rinse) with 10 min. of shaking per rinse. Check the final rinse to verify that it is not acidic. If it is, rinsing should be repeated until the pH of the rinse water is above 6. The filters are not dried at 100° C., since they tend to stick together after this procedure, but rather by vacuum drying. The initial vacuum is applied slowly to prevent blistering of the filters. The filters should be stored in an acid washed, dust-proof container.

Preparation of glass and plastic items

All glassware and plasticware are cleaned by the following sequence of steps:
1. Wash with detergent.
2. Rinse with hot tap water.
3. Rinse with 1N $HNO_3$.
4. Rinse with DIRO water.

5. Dry in an oven at 60° C.

A zero headspace extractor as described in the Federal Register article is not necessary since the analysis is not dealing with volatiles.

Preparation of Extraction Fluids

There are two different extraction fluids, made up fresh daily, as needed. The pH is to be checked prior to use.

Extraction fluid #1: This fluid is used when the pH of water in contact with the sample is <5.0. This fluid is made by adding 5.7 mL glacial acetic acid to 500 mL of D.I. water., adding 64.3 mL of 1.0N NaOH, and diluting to one liter. The resultant pH should be 4.93±0.05.

Extraction fluid #2: This fluid is used when the pH of water in contact with the sample is >5.0 after steps 7.12.1 to 7.12.4 from the Federal Register article. For our application, see step 3 under "Procedure". This fluid is made by adding 5.7 mL glacial acetic acid to water and diluting to one liter. The resultant pH should be 2.88±0.05.

Storage of samples should be at 4° C.

PROCEDURE

Step 1

Separate Solids from Liquids

The filter funnel and vacuum flask are assembled and weighed.

Approximately 5 g of refuse or soil is accurately weighed into the funnel and the weight recorded.

A vacuum is applied for 8 min., drawing the air and fluid into the vacuum flask.

If no liquid is detected in the vacuum flask then go to Step 2. The procedure described in the Federal Register that one must follow (Steps 7.1 through 7.9) to separate solids from liquids in those samples that have free liquids present are not relevant here. Also, Step 7.10 is followed only when there are less than 0.5% solids in the sample. Again, since it is not the case for our present samples (free liquids are not present), this step is not relevant.

Step 2

Determine the Particle Size. By visual inspection make sure there are no particles of a size greater than 0.375 inch. Crush any lumps bigger than this so that they will now fit through a mesh with holes of 0.375 inch (see Step 7.11 in the Federal Register).

Step 3

Determine Alkaline or Acid Buffering. The determination if the materials are alkaline or acid is based on Step 7.12.1 of the Federal Register.

Place 5 g of the soil, 96.5 mL DIRO water and a stir bar into a 250 mL beaker and stir vigorously for 5 min. Measure and record the pH. If the pH is equal to or greater than 5 add 3.5 mL 1N HCl; if the pH is less than 5, add 3.5 mL DIRO. Cover the mixture with a watch glass and rapidly bring to 50° C. on a hot stirplate, stirring constantly. When a temperature of 50° C. is attained, place the beaker and contents into water bath set for 50° C. Allow the mixture to sit for 10 min. Remove the mixture from the water bath, allow the sample to cool to room temperature and read and record the pH. If the pH is less than 5, use Extraction Fluid #1 for Step 4. If the pH is greater than 5, use Extraction Fluid #2.

Step 4

Extraction. Weigh 2 g (dry weight) of soil into an extraction vessel. Add 40 mL (20×soil weight) of the previously determined extraction fluid. Make sure most of the carbon dioxide gas has escaped before sealing the extraction vessel by allowing the vessel to stand open for 30 min. After capping the vessels, disk) to agitate the solution. Rotation speed is 30±2 RPM, for 18 hrs.

Step 5

Sample Preparation. Filter the soil extract/mixture through an acid washed GF/F filter. Transfer the filtrate to a sample vial and (a) analyze for total chromium using atomic absorption spectrometry and (2) analyze spectrophotometrically for hexavalent chromium.

DESCRIPTION OF THE INVENTION

Treatment of Soils Containing Cr(VI)

The solid residues which are the subject of this invention are soils contaminated with unacceptably high Cr(VI) levels. Typically such soils result from the dumping of chromium-laden lime that is a byproduct of the chromium ore roasting process. Such soils often contain calcium at levels approaching that of pure lime where the calcium generally is in the form of lime. These large levels of calcium make the soil highly alkaline and not at all conducive to bacterial growth. Chromium levels in these contaminated soils are variable and can be in the range of from several tens of milligrams per liter to several hundreds of milligrams per liter of chromium.

Reducing the pH of such Cr (VI)-laden solid residues is the first prerequisite of our invention so that the soils can support microbial growth. Generally it is desirable to reduce the pH to a range between about 6.5 and about 9.5, although, as will become clear in subsequent elaboration, initial acid treatment generally is desirable to afford a pH in the 7.0–8.5 range. The nature of the acid is unimportant when viewed solely from the aspect of its ability to reduce the pH. Thus, neutralization may be accomplished by the addition of one or more acids which may be either a mineral acid or an organic acid. An organic acid, such as acetic acid or lactic acid, is advantageous in that it acts simultaneously in neutralizing base and providing a carbon source to aid growth and metabolism of microorganisms. A mineral acid such as sulfuric acid is beneficial since its acidic properties are complimented by its being a source of sulfate, a necessary nutrient for the growth of sulfate reducing bacteria. Similarly, phosphoric acid would provide phosphate, a nutrient often necessary for microbial proliferation and sometimes naturally lacking in the soil.

Unfortunately, some of the aforementioned acids have the disadvantage of forming low solubility calcium salts which tend to clog, or reduce the porosity of, the soil impeding liquid permeation. For example, calcium sulfate is soluble only to the extent of about 0.2–0.3 grams per hundred mL of water, and calcium phosphate is even more insoluble. The degree of clogging depends not only upon the solubility of the resulting calcium salts but also on the conditions under which they are formed. For example, concentrations of under about 15 volume percent acetic acid appear to minimize clogging, whereas use of sulfuric acid requires concentrations under about 1 percent weight/volume. In many aspects hydrochloric acid is a desirable mineral acid since calcium chloride is quite soluble allowing the acid to be used at concentrations up to about 6 molar. From what has been said it should be clear that the kind of acid used is susceptible to great variation, depending upon whether it is sought as a nutrient source as well as an acid, and the concentrations at which the acid may be used will depend not only on the acid but also on the alkalinity and calcium content of the soil being treated.

Because not all of the alkaline materials in the solid residue can be neutralized immediately, the phenomenon of "alkaline rebound" almost invariably accompanies initial acidification. That is, after treatment with acid to a given pH it is noted that the pH gradually rises to its former highly alkaline state. Consequently, a single treatment with acid generally will not suffice and a schedule of acid treatments needs to be worked out in order to achieve a time-stable pH. In other words, there will be more than one cycle of acid treatment. In general, as will be seen below, several applications of anaerobic microorganisms also are necessary for the success of this invention, and scheduling frequently will involve alternate acidification and anaerobic microorganism application treatment.

As alluded to previously, the soil often will not contain all of the necessary nutrients in amounts needed to sustain microbial growth. In the most general case a carbon source will need to be provided which may arise from the acid treatment where a carboxylic acid is used. Phosphate, nitrogen, trace elements, and sulfate also may need to be added in order to provide a hospitable growth environment for the anaerobic microorganisms later applied to the soil.

It is necessary to provide sufficient sulfate in the aqueous residue to make the fermentation effective in reducing soluble Cr(VI) to levels under 0.01. In fact, it has been found that for effective chromium removal soluble sulfate must be present in the liquid aqueous residue in an amount of at least 10 millimoles per liter. Sulfate may be added as the acid, sulfuric acid, or as various sulfate or bisulfate salts, such as ammonium sulfate, sodium sulfate, potassium sulfate, magnesium sulfate, sodium acid sulfate, potassium acid sulfate, and so forth. The use of ammonium sulfate is especially convenient.

The solid residue whose pH has been adjusted to between 6.5 and 9.5 and containing a carbon source and other nutrients, where appropriate, such as sulfate and phosphate, is then inoculated with a hydrogen sulfide-producing anaerobic microorganisms which is not methanogenic. The most common hydrogen sulfide-producing anaerobes are sulfate reducing bacteria arising from the genus desulfovibrio, such as D. vulgaris, D. desulfuricus and D. baculatus; species of the genus Desulfobulbus such as D. proponicus; anaerobes of the genus Desulfobacter, such as D. postgatei; and members of the Desulfotomaculum genus, such as D. nigrificans. It is to be understood that both the genera and specie cited above are merely illustrative of sulfate-reducing anaerobes which may be used in the practice of our invention, and many more such examples of suitable anaerobes will be readily recognized by the skilled worker.

Among the convenient sources of suitable hydrogen sulfide producers may be mentioned beds of rivers, creeks, and other bodies of water where sulfate is present. Septic tanks and marine environments also may be fruitful sources of sulfate-reducing anaerobes. However, a saline source, such as an estuary, marine environment or saline lake is the preferred source since it will have a greater likelihood of yielding a salt-tolerant consortium.

Suitable microorganisms may be isolated by taking a sample from a saline body of water, such as a saltern, brine pool, salt lake, or marine or estuarine environment and adding the sample to a nutrient broth containing essential mineral salts, a carbon source such as an acetate, lactate, or molasses and a high (i.e. 5–15% by weight) concentration of a mineral salt such as sodium chloride, sodium sulfate, calcium chloride and the like. The broth container will be designed to exclude oxygen so that the microorganisms are grown under anaerobic conditions.

Because of alkaline rebound a viable population of anaerobic bacteria can not be sustained, at least in the initial stages of this treatment. In addition, the initial high levels of chromium are themselves toxic to the bacteria and lead to their death. But even in death the microorganisms reduce the level of Cr (VI) via release of intracellular sulfide, electron transfer from oxidizable intracellular constituents such as reducing sugars and sulfhydryl-containing proteins, and, to some extent, absorption of chromium by the cell wall. It has been observed that when the Cr (VI) level is reduced to approximately 200 ppm the anaerobes can overwhelm the metal toxicity, remain viable, and establish an active population which ultimately reduces the Cr (VI) level to a point where the solid residue readily passes the EPA test.

From the foregoing description it should be readily apparent that neither a single treatment of acid nor a single dosage of anaerobes will suffice in reducing Cr (VI) levels to an acceptable point where a solid residue is being treated. Instead our invention will require a repeated sequence of acid treatment followed by application of anaerobic microorganisms until the soil is sufficiently neutralized as to maintain the pH in the 6.0–8.5 range and Cr (VI) levels are reduced to at least 200 ppm, two conditions which form a necessary criterion for a self-sustaining anaerobic population. A complete cycle of acid-anaerobe treatment may last from several hours to several days, although more typically a cycle is at least one day long. So, for example, one can apply acid over a 12 hour period and then anaerobic microorganisms over a similar period to establish a one-day cycle. The length of the cycle and the number of cycles necessary to deplete Cr (VI) will depend sensitively upon the nature of the soil, the amount of Cr (VI) it contains, the permeation characteristics of the solid, its total alkaline content, and so forth.

Similarly, the method of application also will depend upon the aforementioned factors as well as the depth of contamination by Cr (VI) in the soil. One method of application would be surface spraying with the appropriate acid or mixture of acids followed by flooding with hydrogen sulfide-producing anaerobe-laden sludge. Such surface treatment is adequate where the depth of contamination is not great and/or where the soil permits ready percolation or permeation of the liquid. However, where the diffusivity of the acids and the anaerobes in the residue is low then it may be necessary to dig wells or shafts at various points and pump in the acid and anaerobe-laden sludge at various levels in order to ensure adequate treatment.

Another important variant is one where an ancillary agent is added to immediately reduce the Cr (VI) levels so as to facilitate microbial growth by lessening Cr (VI) toxicity. In this regard it may be quite helpful to add a water soluble source of sulfide ion, $S^=$, such as a sulfide salt of an alkali metal, during 1 or more cycles of the treatment so as to effect an immediate and precipitous decline of Cr (VI). The nature of the sulfide is immaterial so long as it is water soluble and a good source of sulfide ion. Alkali metal sulfides are convenient to use, and may be added in aqueous solution after pH adjustment and either concurrent with or, preferably, prior to inoculation with the anaerobic microorganism. Multiple additions may be more effective than just a single larger dose.

Subsurface Extraction of Cr(VI)

The invention will be useful particularly where the Cr(VI) is tied up by the lime resulting from the roasting of chromium ore. Thus, the typical situation finds the Cr(VI) in an essentially solid form in the soil from which it must be separated and treated according to the invention. The chromium is removed from the lime and enters solution during the pH adjustment by treatment with an acid. The Cr(III) produced by reducing Cr(VI) with sulfate-reducing anaerobic bacteria is precipitated as the hydroxide and either separated or left in the place in the soil. If the Cr(VI) is present in the soil in a soluble form, it can be more readily dissolved but it is still necessary to gain access to the Cr(VI) so that it can be converted to the insoluble Cr(III). While it is at least conceptually feasible to excavate and treat the soil and then return the treated soil to the excavated pit, the cost of doing so is believed to be prohibitively expensive. Consequently, in one embodiment the present invention is directed to the conversion of Cr(VI) to Cr(111) while a portion of the chromium remains in place in the soil.

It is difficult to establish conditions under which the microorganisms are able to reduce the Cr(VI) to Cr(III) when the Cr(VI) is located under the surface of the soil. This requires that the concentration of the chromium be relatively low, say up to about 200 ppm, to avoid the inhibition of the action of the microorganisms. The pH must be in a suitable range, preferably about 6.5 to 9.5. Also, the nutrients necessary for the microorganisms to grow and to produce hydrogen sulfide must be present. There must be sufficient sulfates present, preferably at least 10 millimoles per liter of the solution of Cr(VI) which is being treated. Other nutrients such as phosphate, nitrate, and trace elements must be present or else they must be added. It will be apparent that when an indeterminate amount and concentration of Cr(VI) is present below grade, it is most important to be able to measure the amount of Cr(VI) and the degree to which it has been converted to Cr(III). Therefore, portions of the Cr(VI) will ordinarily be removed from the soil for treatment by dissolving the Cr(VI) to form an aqueous solution. It can then be treated to reduce Cr(VI) to Cr(III) and then reinjected into the soil from which it came. In practice, this may be done by dissolving the Cr(VI) by injecting an acid solution into the soil which will separate the Cr(VI) from the lime and provide an aqueous solution which can be treated above grade. Of course, the concentration of Cr(VI) must not be too high since above about 200 ppm the microorganisms are inhibited and the reduction to Cr(III) will be slowed unacceptibly or will cease. Consequently, the concentration and rate of acid injection will be adjusted so that the pH will be within the desired range and not too much Cr(VI) will be dissolved. The solution may be contacted with the microorganisms in a vessel above grade along with added nutrients as required for a period of time which is suitable for reduction of the Cr(VI) to Cr(III) to the desired level.

The degree of reduction may be varied if a continuous recirculation is used so that the solution returned to the soil is moved through the soil toward the point from which the solution is withdrawn to supply the above grade treatment vessel. Such a method is considered preferable since it permits the constant adjustment of the solution composition. The use of a batch process is possible but is not preferred since control of the reduction of Cr(VI) to Cr(III) would be more difficult.

The process required the injection of acid to reduce the pH and to release the Cr(VI) from the lime to which it is bound. Therefore, the process inherently produces calcium salts of the acid used and these salts will inhibit the growth of many microorganisms. Also, the salts potentially may plug the soil if their solubility is low as is the case with calcium sulfate. Thus, the acid of choice is often HCl since calcium chloride is quite soluble and should avoid serious plugging problems. Other acids which do not produce salts of low solubility could be substituted.

Selection of Microorganisms Resistant to High Salt and pH

One approach to solve the problem of growth and metabolism of sulfate bacteria under conditions of high salinity is to develop adapted microorganisms. One may start with a mixed culture of sulfate reducing microorganisms obtained from a marine environment. These sulfate reducing bacteria are adapted to an environment of moderate salinity (approximately 3% w/v) and a pH of approximately pH 8.0. The microorganisms are first cultured in a standard medium used for isolation of sulfate reducing bacteria, but including sea salts equivalent to the salinity of the marine environment. The bacteria would then be subcultured into an identical medium but with the pH adjusted to pH 9.0. Three subsequent subcultures would be made over a period of 2 to 6 weeks per subculture into medium containing sea salts at pH 9.0. Following adaption to pH of 9.0 the cultures would then be adapted to high salinity, especially divalent cations such as calcium. At two to six week intervals four-fifths of the fermentation broth is discarded, along with suspended bacteria. The discarded medium is replaced with medium supplemented with the desired salt (in one case, calcium acetate, in another, calcium chloride) that will yield an increase in ionic strength by 50%. The ability of the microorganisms to thrive under the increasing salt concentrations is monitored by measuring the concentration of hydrogen sulfide in the liquid phase or the gas phase above the liquid. Alternatively, sulfate consumption can also be monitored. Concentrations of greater than 100 ppm hydrogen sulfide in the gas phase are considered a positive sign of adaption. This discarding of spent medium and addition of salt is continued until microorganisms able to tolerate the particular salt concentration, e.g. 7.5% (w/v) $CaCl_2$, are obtained.

A second approach, which may be used in conjunction with the first, is to obtain microorganisms from a specialized environment where it would be expected that microorganisms able to tolerate high salinities, as well as alkaline conditions, might be more readily obtained. Such environments include alkaline soda lakes, such as Big Soda Lake, an alkaline, saline lake in western Nevada, evaporative saline lakes such as the Great Salt Lake, Utah, and alkaline hot springs as are found in Yellowstone National Park, Wyoming. The organisms would be cultured as described above, except that the initial culturing will employ salts and pH similar to the microorganisms natural environment, including a carbon source and sulfate.

Once strains of sulfate reducing bacteria were obtained by these methods that could tolerate high salinities, e.g. $CaCl_2$ concentrations greater than 6% (w/v), and could tolerate pH levels of greater than pH 9.0, they would be adapted to tolerate high chromium levels by a method similar to that for increasing salt tolerance of marine organisms. The sulfate reducing bacteria would be first cultured in an alkaline (pH 9.0) and saline ($CaCl_2$ 6.0% w/v) medium that does not contain any hexavalent chromium. At two to six week intervals, four-fifths of the culture medium would be discarded and replaced with medium supplemented with 10 ppm Cr(VI). This procedure would be repeated with an increase in the Cr(VI) concentration of 10 ppm, i.e. 10 ppm in the first subculture, 20 ppm in the second subculture, 30 ppm in the third subculture, until a concentration of 200 ppm in the culture medium was obtained.

EXAMPLE I

The solid residues tested were soil samples from a state superfund site in Jersey City, N.J., having high levels of Cr(VI) in the residue and the leachate leaving the site to surface runoff and groundwater flow. Twenty grams of residue were slurried in glass vials with 20 mL distilled water and acetic or sulfuric acids were added to adjust the pH of the residue to 7.5. Additional aliquots of acid were added over a two-day period to neutralize the residue prior to addition of anaerobic bacteria so as to allow time for dissolution and complete neutralization of the associated alkalinity. Enrichment cultures of anaerobic sulfate-reducing bacteria were used to inoculate the vials and bacteria were grown in a medium of organic acids and ammonium sulfate as would be prepared on-site in septic tank-like reactors. The medium contained (in g/L): 1.0, sodium lactate; 1.0, sodium acetate; 5.0, ammonium sulfate; 0.2, potassium phosphate (monobasic); 0.2, magnesium sulfate; 0.1, calcium chloride; 0.1, yeast extract; 0.1, sodium thioglycollate; 0.05, ferrous chloride. As a comparison to bacterial inoculation, a solution of sodium sulfide was added in an amount to give a final concentration of 0.5 weight-volume percent in order to reduce and precipitate chromium. The vials were incubated at 20° C. for 33 days.

The addition of either acetic or sulfuric acids to neutralize the residue resulted in increased solubilization of chromate, but the pH continually rose after the initial acid addition indicative of the slow diffusion of the acid into the residue particles resulting in further dissolution of the metal hydroxide. More acid was added after two days incubation to again adjust the pH to a value of 7.5. Further inoculations with anaerobic bacteria or distilled water were made after 14 and 21 days incubation to bolster the original inoculum that may have been inhibited by the increase in pH and high chromate concentration. Results are summarized in Table 1. Analysis of chromate was performed by the diphenylcarbazide method (Standard Methods for the Examination of Water and Waste Water, 14th Edition, 1976, American Public Health Association, Washington, D.C., method 192). A stock solution of chromate was prepared by dissolving 1396.5 mg of sodium chromate in a liter of distilled water (1000 mg chromate/L). A solution of diphenylcarbazide was prepared by dissolving 250 mg of sym-diphenylcarbazide in 50 mL of acetone. This solution was stored in a brown bottle and was replaced with a fresh solution when it became discolored. A calibration curve was prepared by adding 1, 2, 4, 6, 8, and 10 mL of the chromate stock solution to 6×100 mL volumetric flasks respectively. The six solutions correspond to 10, 20, 40, 60, 80 and 100 mg/L concentrations of chromate. One mL of the sample to be analyzed was added to a 100 mL volumetric flask (if the sample contains more than 1000 mg/L of chromate, further dilution will be necessary). To all the standard and sample flasks 100 µL of concentrated sulfuric acid was added. The volume in the flasks was then made up to 100 mL. Two mL of the diphenylcarbazide solution was added to all sample and standards flasks. The flasks were capped and mixed well and then allowed to sit for 10 mins before measurement of the adsorption at 540 nm using distilled water as the reference. A standard curve was then plotted from the adsorption of the standard solutions and the concentration in the sample flasks determined by cross matching with this curve. To make the test more sensitive, more of the sample could be added to the volumetric before making up the volume to 100 mL.

TABLE 1

| Reduction of Chromate in Solid Waste Residue by Sodium Sulfide and Anaerobic Bacterial Inoculate | | | | | | | | |
|---|---|---|---|---|---|---|---|---|
| | Chromate (mg/L) | | | | | | | |
| | Control | | | Sulfide | | | Bacteria | |
| Days | Water | Acetic Acid | Sulfuric Acid | Water | Acetic Acid | Sulfuric Acid | Acetic Acid | Sulfuric Acid |
| 0 | 61 | 2300 | 600 | 81 | 2050 | 1000 | 2100 | 1000 |
| 1 | 64 | 2400 | 700 | 0 | 0 | 0 | 1300 | 1050 |
| 2 | 65 | 1100 | 840 | 0 | 1.5 | 0 | 740 | 1000 |
| 12 | 91 | 1570 | 1950 | 0 | 11.5 | 7.5 | 500 | 700 |
| 14 | 95 | 1520 | 1900 | 0 | 20.5 | 29.5 | 490 | 520 |
| 16 | 61 | 920 | 1120 | 0 | 0 | 0 | 320 | 330 |
| 19 | 64 | 1040 | 870 | 5 | 0 | 0 | 300 | 350 |
| 21 | 64 | 1020 | 854 | 4 | 0 | 0 | 200 | 240 |
| 23 | 64 | 946 | 730 | 4 | 0 | 0 | 136 | 172 |
| 28 | 66 | 900 | 730 | 4 | 0 | 0 | 0 | 0 |
| 30 | 66 | 880 | 730 | 5 | 0 | 0 | 0 | 0 |
| 33 | 68 | 900 | 730 | 5 | 0 | 0 | 0 | 0 |

The addition of sodium sulfide resulted in a rapid reduction and precipitation of chromium in the slurries in both neutralized and unneutralized vials. In the neutralized slurries there was a gradual increase in chromate from a value of 0 mg/L at one day to 25 mg/L at 14 days incubation, probably due to the dissolution of more residue by the acids with further release of chromate. The addition of further sulfide after 14 days to the neutralized slurries once again resulted in rapid reduction and precipitation of the chromate with no further increase in chromate following this second addition. There was a more gradual increase in the chromate levels following addition of reductant to the unneutralized slurry as there was a very slow dissolution of residue in the absence of acid addition. The unneutralized slurry was not reduced a second time with additional sulfide.

In the vials inoculated with anaerobic sulfate reducing bacteria there was a small but rapid drop in the chromate levels following each inoculation. However, it was not until the chromate level had been reduced to about 200 mg/L at 21 days that the anaerobic bacteria were able to survive and actively reduce the chromium in solution to near 0 mg/L. Prior to that point the inoculum was rapidly oxidized from a black to a light brown color. When the last inoculum was made, however, the inoculum remained black with the band quickly spreading down the vial reducing it from a light brown to a dark color, corresponding to the removal of chromium from solution.

The foregoing results suggest that multiple inoculations of anaerobic bacterial microorganisms will be needed to reduce the chromate level to about 200 mg/L at which point the sulfate-reducing bacteria can survive and completely reduce the chromate-containing residue. The addition of reducing agents such as sodium sulfide or sulfite would help the anaerobic population establish themselves in the neutralized residue and would lead to a complete reduction of Cr(VI).

Analysis of the interstitial water in the treated and untreated vials showed that the hexavalent and trivalent chromium had been removed from solution and that the bacteria were even more efficient than sodium sulfide in achieving this goal. By interstitial water is meant the aqueous fraction that occupies the void space between the solid particles in the treated residue material. This water is obtained by high speed centrifugation or mechanical pressing of the residue material. Analysis of chromate in the interstitial water was done by the diphenylcarbazide technique. Chromium VI concentrations were calculated from these values. Chromium III concentrations were determined by ion chromatography and total chromium was determined by Atomic Adsorption Spectroscopy. Results are summarized in Table 2.

TABLE 2

Chromium Species Present in the Interstitial Water of Treated Solid Residue

| Sample | Concentration (mg/L) | | | |
|---|---|---|---|---|
| | Chromate | Cr(VI) | Cr(III) | Total |
| Cr. | | | | |
| Control (no acid) | 178 | 79 | <1.0 | 71 |
| Acetic Acid | 1750 | 784 | <1.0 | 840 |
| Sulfuric Acid | 1350 | 605 | <1.0 | 597 |
| Control/Sulfide | <1.0 | <1.0 | 1 | 1 |
| Acetic/Sulfide | <1.0 | <1.0 | 3 | 3 |
| Sulfuric/Sulfide | <1.0 | <1.0 | 1 | 1 |
| Acetic/Bacteria | <1.0 | <1.0 | <1.0 | <1.0 |

TABLE 2-continued

Chromium Species Present in the Interstitial Water of Treated Solid Residue

| Sample | Concentration (mg/L) | | | |
|---|---|---|---|---|
| | Chromate | Cr(VI) | Cr(III) | Total |
| Sulfuric Bacteria | <1.0 | <1.0 | <1.0 | <1.0 |

A Toxicity Characteristic Leaching Procedure (TCLP) leach test previously described was conducted on the treated residue to determine whether it passed the requirements for listing as a non-hazardous chromium-containing waste. The results of the test indicated that the chromium in the treated vials is in a non-leachable form and may be considered a non-hazardous waste; see Table 3. Total chromium was determined by Atomic Adsorption Spectroscopy.

TABLE 3

Solid EPA Leach Test of Treated Residue

| Sample | Concentration (mg/L) |
|---|---|
| Cr | |
| Control (No Acid) | 260 |
| Acetic Acid | 160 |
| Sulfuric Acid | 190 |
| Control/Sulfide | 2.1 |
| Acetic/Sulfide | 1.7 |
| Sulfuric/Sulfide | 1.7 |
| Acetic/Bacteria | <0.1 |
| Sulfuric/Bacteria | <0.1 |

A second set of experiments were run with other samples of solid waste residue from the same superfund site. Once again, multiple additions of acid and bacteria were required to obtain the correct conditions within the residue, but once this was achieved the bacteria were successful in reducing the hexavalent chromium to below detectable limits as summarized in Table 4.

TABLE 4

Solid Waste Reduction of Chromium in Residue by Anaerobic Bacteria Following Acid Neutralization

| | Chromate Concentration (mg/L) | | | | | |
|---|---|---|---|---|---|---|
| | Control | | | Bacteria | | |
| Days | No Acid | Acetic Acid | Sulfuric Acid | No Acid | Acetic Acid | Sulfuric Acid |
| 0 | 88 | 750 | 1200 | 385 | 700 | 1125 |
| 2 | 125 | 925 | 1225 | 225 | 1100 | 1175 |
| 5 | 125 | 1260 | 2060 | 315 | 1325 | 2150 |
| 7 | 140 | 1260 | 2125 | 317 | 1275 | 2150 |
| 10 | 142 | 1250 | 2110 | 312 | 1185 | 2135 |
| 12 | 148 | 1235 | 2135 | 320 | 1160 | 2125 |
| 15 | 145 | 1235 | 1975 | 255 | 1050 | 1800 |
| 18 | 135 | 1020 | 1925 | 265 | 1050 | 1800 |
| 25 | 137 | 1020 | 1540 | 107 | 207 | <0.1 |
| 27 | 137 | 1040 | 1580 | 107 | 220 | <0.1 |
| 32 | 147 | 852 | 1310 | 83 | <0.1 | <0.1 |
| 34 | 150 | 945 | 935 | 96 | <0.1 | <0.1 |
| 39 | 149 | 1475 | 1500 | 97 | <0.1 | <0.1 |

EXAMPLE II

The following exemplifies bioremediation of soil in a plug flow reactor. Soil contaminated with large quantities of lime, calcium carbonate, and chromate was loosely packed into a glass column 0.7 cm ID and 17 cm high. The soil had an alkalinity requiring 6 milliequivalents of hydrochloric acid for neutralization of 1 gram (dry weight) to pH 7 and contained about 950 ppm hexavalent chromium and 16,000 ppm total chromium.

To the top of the column containing 5.1 gram (dry weight) of soil was added 1.5 mL of 1 molar hydrochloric acid which caused the evolution of a gas. Water was then added, followed by an inoculum of sulfate-reducing anaerobic microorganisms. A black layer formed at the top of the column about 1 cm deep indicating the formation of metal sulfides. Below this layer was an off-white precipitate dispersed between the particles of soil with an appearance similar to that of chromium hydroxide. Upon repeating the cycle of acid, water, and bacteria the black layer first was bleached but then reformed with a greater thickness. The off-white layer also was reformed at a greater depth indicating further formation of $Cr(OH)_3$.

EXAMPLE III

To demonstrate the ability of this process to shorten the leaching process the following experiment was carried out. Into a glass column, 2.5 cm ID × 20.0 cm long, was added 61.29 g dry weight (79.1 g wet weight) of Cr(VI)-laden lime. The temperature was ambient, around 23° C. Water was pumped through this solid residue from top to bottom at a rate of about 0.45 L per day. After 131 days, the concentration of Cr(VI) was still 1.28 ppm. At this point, fermented medium plus anaerobic sulfate reducing bacteria were passed through the solid residue at a rate of 140 mL per day. The concentration of Cr(VI) in the first 33 mL of effluent transiently rose to a value of 60.2 ppm. The next 192 mL possessed a Cr(VI) concentration of 0.031 ppm. The next 140 mL collected contained less than 0.0002 ppm Cr(VI). Based on the data in the following Table, it would be expected that Cr(VI) would have bled from the lime for years if water leaching had been continued, while the bacterial treatment immobilized the Cr(VI) in the lime.

TABLE 5

| Day | Water Effluent | |
|---|---|---|
| | pH | Cr(VI) ppm |
| 4 | 10.11 | 84 |
| 24 | 11.60 | 33 |
| 44 | 10.78 | 9 |
| 64 | 10.94 | 4.42 |
| 84 | 10.62 | 2.54 |
| 104 | 11.04 | 1.75 |
| 125 | 10.54 | 1.40 |
| 131 | 10.70 | 1.28 |
| Water replaced with medium containing anaerobic sulfide reducing bacteria. | | |
| 131 | 10.83 | 60.2 |
| 132 | 10.85 | 0.031 |
| 132 | 9.75 | <0.0002 |

EXAMPLE IV

The following test demonstrates that chromium bioremediated soil has been immobilized and will not be leached from the soil.

The Cr(VI)-laden lime was neutralized by the following procedure. Into an open beaker was placed 500 g (wet weight; equivalent to 374 g dry weight) of the Cr(VI)-laden lime. To this material was slowly added, with stirring, 848 mL of 6N HCl. No additional water was needed to create a slurry. The pH was initially low but after about sixteen days the pH stabilized at 7.4. The supernatant in contact with the neutralized soil possessed a Cr(VI) concentration of 2461 ppm. The calcium concentration was 7.93% w/w. The supernatant was separated from the precipitate by centrifugation. The weight of the supernatant was 543 g. The wet weight of the residue was 942.4 g. On a weight basis, the ratio of supernatant to residue was therefore 0.576 to 1.000. Using this information, we could readily reconstitute a representative sample of neutralized material on an as needed basis by mixing 0.576 g neutralized supernatant with 1 g neutralized solid residue.

We prepared a seed culture by growing an anaerobic sulfate reducing consortia obtained from the sludge on the bottom of Baltimore harbor on a solution containing both 3 mL of 20% w/v (10% solids) molasses and 2 mL of a 5.22% w/v solution of the sodium salt of 1-lactic acid per 100 mL culture medium. The resulting consortium reduced Cr(VI) using either lactate or molasses as a carbon source.

The bioremediation was performed as follows. Into a one-liter graduated cylinder fitted with a ground glass joint and a three-hole black rubber stopper was placed 200 mL of five fold concentration nutrient medium (see Table below), 31.71 g of the above mentioned neutralized solid residue, 18.32 g of the above mentioned liquid residue, 20 mL of the lactate solution, 10 mL of the phosphate solution and 720 mL DIRO water. The system was purged with nitrogen using glass tubes inserted into the stopper. A similar experiment was performed using 30 mL of 20% w/v molasses as the carbon source, replacing the lactate. The pH was maintained at pH 8.0±0.5. The experiment was left undisturbed for two months.

TABLE 6

Medium for Sulfate Reducing Bacteria

| Compound | Mol. Wt. | mMol/L | g/L | 5-Fold Conc., g/L |
|---|---|---|---|---|
| Na Acetate | 82.03 | 12.2 | 1 | 5 |
| $Na_2SO_4$ | 142.04 | 28.2 | 4 | 20 |
| $(NH_4)_2SO_4$ | 132.14 | 3.79 | 0.5 | 2.5 |
| $MgSO_4$—$7H_2O$ | 246.48 | 1.01 | 0.25 | 1.25 |
| $CaCl_2$—$2H_2O$ | 142.91 | 0.70 | 0.1 | 0.5 |
| Yeast extr | — | — | 0.1 | 0.5 |
| DiNa EDTA | — | — | 0.05 | 0.25 |
| $FeSO_4$ | 278.02 | 0.180 | 0.05 | 0.25 |
| Na Thioglycolate | — | — | 0.05 | 0.25 |
| Thamer's trace elements | — | — | 1.0 mL | |

Phosphate solution:
6% w/v dibasic potassium phosphate
2% w/v monobasic potassium phosphate The following acid digestion procedure was used to dissolve the chromium-laden lime or remediated solid residue for determination of total Cr. When a few grams of Cr(VI)-laden lime from a New Jersey site is dispersed in one L of 2N HCl the solids dissolve. What is formed is a clear, easily measured solution of Cr salts and a very light film of what appears to be silica.

a) The material to be tested was lyophilized and ground to a fine powder using a mortar and pestle.

b) 826.7 g (799.3 mL) of 2N HCl was added to a squat Erlenmeyer fitted with a glass stopper. To this was added one g dried ground residue. The suspension was stirred using a magnetic stir bar. Unremediated residue turned from a slightly cloudy yellow-green color to an essentially clear solution in about 5 min. The suspension was stirred overnight during which time virtually complete dissolution appeared to occur, yielding the bright yellow of Cr(VI). In contrast, remediated residue had a grey-green appearance.

c) The supernatant was assayed for Cr(VI) using the diphenylcarbazide method and total Cr by atomic absorption.

The unremediated neutralized Cr(VI) laden lime possessed a total acid soluble Cr concentration of 1.7% and an acid soluble Cr(VI) concentration of 0.89%. The TCLP extract (near neutral conditions) has a Cr(VI) concentration of 103 ppm. After bioremediation the value for total acid soluble Cr in the solid residue is essentially unchanged at 1.6%. In contrast, the value for Cr(VI) drops dramatically after bioremediation. After bioremediation using lactate as a carbon source, the solid residue possessed an acid soluble Cr(VI) concentration of only 0.011% and a TCLP extract (neutral conditions) concentration of <0.0002 ppm. The corresponding values obtained when molasses is used as a carbon source are not significantly different from the lactate results, with values of 0.002% and <0.0002 ppm, respectively.

EXAMPLE V

Typical Operation of A Field Unit

When applied in the field, where Cr(VI) laden lime is to be processed, the operation of the system for biological reduction of Cr(VI) to Cr(III) results in the formation of high quantities of salts, e.g. 8.0% (w/v) calcium ion. This salt formation is a direct result of the neutralization of the highly alkaline lime. It is therefore advantageous to employ sulfate reducing bacteria that are able to tolerate as high a pH as possible as well as tolerate high salts. The higher pH the process is performed at the less acid that is required and the less salt is produced. The nature of the salt produced is dependent upon the acid used for neutralization. For example, when the neutralizing agent is HCl, $CaCl_2$ is formed. When the neutralizing agent is acetic acid, calcium acetate is formed. The partial neutralization of the lime-containing chromium waste results in the formation of a liquid that has a high salinity, i.e. 8.0% (w/v) calcium ion, a high pH, i.e. pH 9.0, and a high concentration of Cr(VI), i.e. 2500 ppm. This liquid is withdrawn from the contaminated site by means of recovery wells and is then pumped to a reservoir. The aqueous liquid is then pumped to the biological reactor where additional carbon source and sulfate have been added to maintain an active population of high pH, high salt tolerant, and high chromium resistant sulfate reducing bacteria. Within the biological reactor, the soluble Cr(VI) is reduced to the insoluble Cr(III) in the presence of the high salinity and high pH. The insoluble Cr(III) precipitates as $Cr(OH)_3$ and settles to the bottom of the biological reactor where it can be drawn off as a sludge. The remediated aqueous stream containing active, adapted sulfate reducing bacteria is then recirculated into the contaminated soil by means of injection wells and/or infiltration trenches and will result in in-situ reduction and precipitation of the Cr(VI) remaining in the soil. As the sulfate reducing bacteria are especially adapted to the unique conditions of the alkaline, saline contaminated residue, they can proliferate within the soil and the resulting sulfide will permeate the soil particles to reduce chromium. If just water flushing was used to remove the residual Cr(VI), then very large volumes of water would have to be used to treat the contaminated soil. When the aqueous medium containing the adapted sulfate reducing bacteria is flushed through the contaminated soil, less than 100th the volume of fresh water is required to remove or reduce and precipitate Cr(VI) in the soil.

What is claimed is:

1. A method of immobilizing chromium in calcium and chromium containing alkaline solid residue from chromium ore roasting located below the surface of the soil comprising:
    (a) injecting a first aqueous solution into soil contaminated with said solid residue at a first location to contact said residue, said first solution containing sufficient acid to provide a pH of 6.5 to 9.5;
    (b) withdrawing a second aqueous solution containing dissolved Cr(VI) and calcium and having a high salinity and a pH of 6.5 to 9.5 from the soil at a second location at the same rate as the injection rate of (a);
    (c) contacting said second aqueous solution with sulfate-reducing anaerobic bacteria capable of tolerating high salinity in the presence of a sulfate source sufficient to provide at least 10 millimoles sulfate per liter of said second solution, for a sufficient time to reduce substantially all of the Cr(VI) to insoluble Cr(III);
    (d) separating the insoluble Cr(III) to produce a remediated aqueous solution containing active, sulfate reducing anaerobic bacteria; and
    (e) adding acid as needed to provide a pH of 6.5 to 9.5 and returning the remediated aqueous solution from (d) to the first aqueous solution for recirculating into the contaminated soil to result in in-situ reduction of Cr(VI) in the solid residue to insoluble Cr(III) whereby the insoluble Cr(III) becomes immobilized in the solid residue in the soil.

2. The method of claim 1 wherein the Cr(VI) dissolved in said second aqueous solution of (b) is about 200 ppm or less.

3. The method of claim 1 wherein said acid is hydrochloric acid.

4. The method of claim 1 wherein said acid is acetic acid or lactic acid.

5. The method of claim 1 wherein step (c) includes addition of a sulfate to said second aqueous solution to provide at least 10 millimoles sulfate per liter.

6. The method of claim 1 wherein nutrients are added in step (c) to support the growth of said bacteria.

7. The method of immobilizing chromium located below the surface of the soil comprising:
    (a) injecting a first aqueous solution into soil at a first location to contact the soil, said aqueous solution containing sufficient acid to provide a pH of 6.5 to 9.5;
    (b) withdrawing a second aqueous solution containing dissolved Cr(VI) and calcium and having a high salinity and a pH of 6.5 to 9.5 from the soil at a second location at the same rate as the injection rate of (a);
    (c) contacting said second aqueous solution with sulfate-reducing anaerobic bacteria capable of tolerating high salinity in the presence of a sulfate source sufficient to provide at least 10 millimoles sulfate per liter of said second solution, for a sufficient time to reduce substantially all of the Cr(VI) to insoluble Cr(III);
    (d) separating the insoluble Cr(III) to produce a remediated aqueous solution containing active, sulfate reducing anaerobic bacteria; and
    (e) adding acid as needed to provide a pH of 6.5 to 9.5 and returning the remediated aqueous solution for recirculating into the soil to result in in-situ reduction of Cr(VI) in the soil to insoluble Cr(III)

whereby the insoluble Cr(III) becomes immobilized in the soil below the surface.

8. The method of claim 7 wherein the Cr(VI) dissolved in said second aqueous solution of (b) is about 200 ppm or less.

9. The method of claim 6 wherein said acid is hydrochloric acid.

10. The method of claim 7 wherein said acid is acetic acid or lactic acid.

11. The method of claim 6 wherein step (c) includes addition of a sulfate to said second aqueous solution to provide at least 10 millimoles sulfate per liter.

12. The method of claim 7 wherein nutrients are added in step (c) to support the growth of said bacteria.

13. A method of immobilizing chromium in a calcium and chromium containing alkaline solid residue from chromium ore roasting comprising:

(a) contacting said solid residue with an aqueous acid capable of dissolving Cr(VI) to provide an aqueous solution containing dissolved Cr(VI) and calcium having a pH of about 6.5 to 9.5;

(b) contacting the aqueous solution of (a) with sulfate-reducing anaerobic bacteria capable of tolerating high salinity in the presence of at least 10 millimoles per liter of sulfate and sufficient nutrients to support the growth of said bacteria to reduce Cr(VI) to insoluble Cr(III) in the presence of said solid residue whereby said Cr(III) becomes immobilized in said solid residue; and (c) repeating steps (a) and (b) until substantially all of the Cr(VI) in said residue is reduced to insoluble Cr(III) immobilized in said residue.

14. The method of claim 13 wherein the Cr(VI) in said aqueous solution of (a) is 200 ppm or less.

15. The method of claim 13 wherein said acid is hydrochloric acid.

16. The method of claim 13 wherein said acid is acetic acid or lactic acid.

* * * * *

UNITED STATES PATENT AND TRADEMARK OFFICE
CERTIFICATE OF CORRECTION

PATENT NO. : 5,155,042

DATED : October 13, 1992

INVENTOR(S) : F. Stephen Lupton, Louis J. DeFilippi and James R. Goodman

It is certified that error appears in the above-identified patent and that said Letters Patent is hereby corrected as shown below:

On the title page, item [75], "Louis J. Defilippi, Prospect" should read --Louis J. DeFilippi, Mt. Prospect--.

Attorney, Agent or Firm: "Gerhard H. Fuch" should read --Gerhard H. Fuchs--.

Column 6, line 10: after "vessels" insert --the end-over-end agitator is used (ROTO-TORQUE with serum bottle--.

Column 18, line 51: delete "and calcium"

Signed and Sealed this

Sixteenth Day of November, 1993

Attest:

BRUCE LEHMAN

*Attesting Officer*   *Commissioner of Patents and Trademarks*